(12) United States Patent
Werbovetz et al.

(10) Patent No.: US 7,211,696 B2
(45) Date of Patent: May 1, 2007

(54) ANTILEISHMANIAL DINITROANILINE SULFANOMIDES WITH ACTIVITY AGAINST PARASITE TUBULIN

(75) Inventors: Karl Werbovetz, Worthington, OH (US); Dan L. Sackett, Washington, DC (US); Manar M. Salem, Columbus, OH (US)

(73) Assignees: The Ohio State University, Columbus, OH (US); National Institutes of Health, Bethesda, MD (US)

( * ) Notice: Subject to any disclaimer, the term of this patent is extended or adjusted under 35 U.S.C. 154(b) by 91 days.

(21) Appl. No.: 10/512,335

(22) PCT Filed: Apr. 23, 2003

(86) PCT No.: PCT/US03/12587

§ 371 (c)(1),
(2), (4) Date: Oct. 20, 2004

(87) PCT Pub. No.: WO03/090678

PCT Pub. Date: Nov. 6, 2003

(65) Prior Publication Data

US 2005/0227982 A1  Oct. 13, 2005

Related U.S. Application Data

(60) Provisional application No. 60/382,965, filed on May 24, 2002, provisional application No. 60/374,727, filed on Apr. 23, 2002.

(51) Int. Cl.
*C07C 211/00* (2006.01)
*C07D 295/04* (2006.01)
*C07D 207/00* (2006.01)
*C07D 265/30* (2006.01)
*A61K 31/00* (2006.01)

(52) U.S. Cl. ............... 564/441; 548/577; 544/159; 514/237; 514/317; 514/408; 514/646

(58) Field of Classification Search ............... None
See application file for complete search history.

(56) References Cited

U.S. PATENT DOCUMENTS

| | | | |
|---|---|---|---|
| 3,880,644 A * | 4/1975 | Beck | 504/218 |
| 4,041,159 A | 8/1977 | Platt et al. | |
| 4,091,096 A * | 5/1978 | Beck et al. | 514/157 |
| 4,104,054 A * | 8/1978 | Beck | 504/333 |
| 4,180,568 A | 12/1979 | Beck et al. | |

FOREIGN PATENT DOCUMENTS

DE          2332979          1/1974

OTHER PUBLICATIONS

Benbow et al. Synthesis and Evaluation of Dinitroanilines for Treatment of Cryptosporidiosis. Antimicrobial Agents and Chemotherapy, 1998, vol. 42 (2), p. 339-343.*

International Search Report for PCT/US03/12587, Nov. 5, 2003.

Benbow, J. W., et al. "Synthesis and of Dinitroanilines for treatment of cryptosporidiosis", 2 pgs., Antimicrobial Agents and Chemotherapy (1998), 42(2), 339-343 and Abstract.

Bhattacharya, Gautam, et al, "Synthesis and Antitubulin Activity of N1-and N4-Substituted 3,5-Dinitro Sulfanilamides against African Trypanosomes and Leishmania", J. Med. Chem. 2004, 47, 1823-1832.

(Continued)

*Primary Examiner*—Sikarl A. Witherspoon
(74) *Attorney, Agent, or Firm*—Calfee, Halter & Griswold, LLP (57) ABSTRACT

Dinitroaniline compounds useful for the treatment of diseases caused by parasitic protozoa in subjects in need of such treatment. The compounds are particularly useful in the treatment of leishmaniasis. The compounds are preferably less cytotoxic to normal cells than oryzalin. Also provided are methods of treating subjects having diseases caused by parasitic protozoa, preferably humans. The method comprising administering a therapeutically effective amount of a dinitroaniline compound of the present invention to a subject in need of such treatment

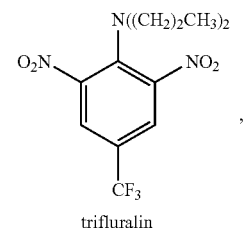
trifluralin

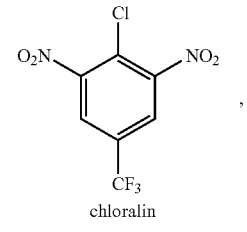
chloralin

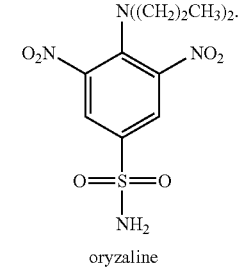
oryzaline

20 Claims, 2 Drawing Sheets

OTHER PUBLICATIONS

Bhattacharya, Gautam, et al, "Antileishmanial Dinitroaniline Sulfonamides with Actiity Against Parasite Tubulin", Bioorganic & Medicinal Chemistry Letters 12 (2002) 2395-2398.

George, Tesmol G., et al, "Antikinetoplastid antimitotic activity and metabolic stability of dinitroaniline sulfonamides and benzamides", Bioorganic & Medicinal Chemistry, 2006, 12 pgs.

Abstract only, Makioka, A., et al, "Effect of dinitroanilline herbicides on the growth of Entamoeba histolytica", 2 pgs., 2003, Journal of Parasitology (2000), 86(3), 607-610.

Werbavetz, Karl A., et al, "Selective Antimicrotubule Activity of N1-Phenyl-3,5-dinitro-N4-di-n-propylsulfanilamide (GB-II-5) against Kinetoplastid Parasites", Mol. Pharmacol 64: 1325-1333, 2003.

Wu, Di et al., Pre-systemic metabolism prevents in vivo antikinetoplastid activity of N1, N4-substituted 3,5-dinitro sulfanilamide, GB-II-150, Life Sciences, 2006, 13 pgs.

Yakovich, Adam J. et al, "Leishmania tarentolae: Purification and characterization of tubulin and its suitability for antileishmanial drug screening", 2006, 8 pgs.

\* cited by examiner

Reagents and conditions: (i) R₁H/reflux, R₁H/MeOH, or R₁H/MeOH/reflux; (ii) PCl₅/CH₂Cl₂; (iii) NH₃/MeOH/50°C; (iv) aniline or propylamine/reflux.

Fig. 3

Scheme 2. Reagents and conditions: (i) ClSO₃H/120°C; (ii) NH₃ in dioxane/ethyl acetate/ -5°C; (iii) dipropylamine/reflux

Fig. 4

Reagents and conditions: (i) Dipropylamine/reflux; (ii) conc. H₂SO₄/50°C; (iii) NH₂OH.HCl/Na₂CO₃/EtOH/reflux.

Fig. 5

ANTILEISHMANIAL DINITROANILINE SULFANOMIDES WITH ACTIVITY AGAINST PARASITE TUBULIN

CROSS-REFERENCE TO RELATED APPLICATIONS

This application claims priority to U.S. Provisional Patent Applications Nos. 60/374,727 filed Apr. 23, 2002, and 60/382,965 filed May 24, 2002, the entirety of each are incorporated herein by reference.

BACKGROUND OF THE INVENTION

There is a general lack of effective, inexpensive chemotherapeutic agents for the treatment of parasitic protozoal diseases that occur in the developing world. These parasitic protozoal diseases include leishmaniasis, including visceral leishmaniasis, mucocutaneous leishmaniasis, and cutaneous leishmaniasis; Chagas disease; human African trypanosomiasis, also known as African sleeping sickness; animal trypanosomiasis; and malaria.

Leishmaniasis currently threatens 350 million men, women and children in 88 countries around the world. The leishmaniases are parasitic diseases with a wide range of clinical symptoms: cutaneous, mucocutaneous and visceral. Visceral leishmaniasis—also known as kala azar is characterized by irregular bouts of fever, substantial weight loss, swelling of the spleen and liver, and anemia (occasionally serious). If left untreated, the fatality rate can be as high as 100%. In mucocutaneous forms of leishmaniasis, lesions can lead to partial or total destruction of the mucose membranes of the nose, mouth and throat cavities and surrounding tissues. These disabling and degrading forms of leishmaniasis can result in victims being humiliated and cast out from society. Cutaneous forms of the disease normally produce skin ulcers on the exposed parts of the body such as the face, arms and legs. The disease can produce a large number of lesions—sometimes up to 200—causing serious disability and invariably leaving the patient permanently scarred, a stigma which can cause serious social prejudice.

The leishmaniases are caused by different species belonging to the genus *Leishmania* a protozoa transmitted by the bite of a tiny 2 to 3 millimeter-long insect vector, the phlebotomine sandfly. Of 500 known phlebotomine species, only some 30 of them have been positively identified as vectors of the disease. Only the female sandfly transmits the protozoan, infecting itself with the *Leishmania* parasites contained in the blood it sucks from its human or mammalian host in order to obtain the protein necessary to develop its eggs. During a period of 4 to 25 days, the parasite continues its development inside the sandfly where it undergoes major transformation. When the now infectious female sandfly feeds on a fresh source of blood, its painful sting inoculates its new victim with the parasite, and the transmission cycle is completed.

The insect vector of leishmaniasis, the phlebotomine sandfly, is found throughout the world's inter-tropical and temperate regions. The female sandfly lays its eggs in the burrows of certain rodents, in the bark of old trees, in ruined buildings, in cracks in house walls, and in household rubbish, as it is in such environments that the larvae will find the organic matter, heat and humidity which are necessary to their development. In its search for blood (usually in the evening and at night), the female sandfly covers a radius of a few meters to several hundreds around its habitat. For a long time, little was known about the transmission cycles of the disease, but over the last few years, field research and the application of molecular biology have enabled substantial progress to be made in understanding the different links in the transmission chain. Moreover, simple new diagnostic techniques have recently been developed which are practical, reliable and inexpensive. These techniques are available to concerned countries for the early detection and rapid treatment of the disease.

The Leishmaniases are related to environmental changes such as deforestation, building of dams, new irrigation schemes, urbanization and migration of non-immune people to endemic areas. It seriously hampers productivity and vitally needed socioeconomic progress and epidemics have significantly delayed the implementation of numerous development programs. This is particularly true in Saudi Arabia, Morocco, the Amazon basin and the tropical regions of the Andean countries.

For many years, the public health impact of the leishmaniases has been grossly underestimated, mainly due to lack of awareness of its serious impact on health. Over the last 10 years endemic regions have been spreading further afield and there has been a sharp increase in the number of recorded cases of the disease. As declaration is obligatory in only 32 of the 88 countries affected by leishmaniasis, a substantial number of cases are never recorder. In fact, of the 1.5–2 million new cases estimated to occur annually, only 600,000 are officially declared In addition, deadly epidemics of visceral leishmaniasis periodically flare up. For example, in the 1990s Sudan suffered a crisis with an excess mortality of 100,000 deaths among people at risk. An epidemic of cutaneous leishmaniasis is ongoing in Kabul, Afghanistan with an estimated 200,000 cases.

Chagas disease has a wide distribution in Central and South America, being found only in the American Hemisphere. It is endemic in 21 countries, with 16–18 million persons infected and 100 million people at risk. The disease is caused by *Trypanosoma cruzi*, a flagellated protozoan parasite which is transmitted to humans in two ways, either by a blood-sucking reduviid bug which deposits its infective feces on the skin at the time of biting, or directly by transfusion of infected blood. Humans and a large number of species of domestic and wild animals constitute the reservoir, and the vector bugs infest poor housing and thatched roofs.

The acute stage of the disease is generally seen in children, and is characterized by fever, swelling of lymph glands, enlargement of the liver and spleen, or local inflammation at the site of infection. But, commonly, there are no acute clinical manifestations, and those infected may remain without symptoms. In about one-third of acute cases, a chronic form develops some 10–20 years later, causing irreversible damage to the heart, esophagus and colon, with dilatation and disorders of nerve conduction of these organs. Patients with severe chronic disease become progressively more ill and ultimately die, usually from heart failure. There is, at present, no effective treatment for such cases.

Rural migrations to urban areas during the 1970s and 1980s changed the traditional epidemiological pattern of Chagas disease: it became an urban disease, as unscreened blood transfusion created a second way of transmission. Between 1960 and 1989, the prevalence of infected blood in blood banks in selected cities of South America ranged from 1.7% in Sao Paulo, Brazil to 53.0% in Santa Cruz, Bolivia, a percentage far higher than that of hepatitis or HIV infection.

Human African trypanosomiasis, known as sleeping sickness, is a vector-borne parasitic disease. *Trypanosoma*, the parasites concerned, are protozoa transmitted to humans by tsetse flies (*glossina*). Tsetse flies live in Africa, and they are found in vegetation by rivers and lakes, gallery-forests and vast stretches of wooded savannah. Sleeping sickness occurs only in sub-Saharan Africa, in regions where tsetse flies are endemic. For reasons as yet unknown, there are many regions where tsetse flies are found, but sleeping sickness is not. The rural populations that live in such environments and depend on them for agriculture, fishing, animal husbandry or hunting are the most exposed—along with their livestock—to the bite of the tsetse fly.

Sleeping sickness affects remote and rural areas where health systems are least effective, or non-existent. It spreads with socio-economic problems such as political instability, displacement of populations, war and poverty. It develops in foci whose size can range from a village to an entire region. Within a given focus, the intensity of the disease can vary considerably from one village to the next.

Human African trypanosomiasis takes two forms, depending on the parasite involved: *Trypanosoma brucei gambiense* (*T.b. gambiense*) is found in central and West Africa. It causes chronic infection, which does not mean benign. A person can be infected for months or even years without obvious symptoms of the disease emerging. When symptoms do emerge, the disease is already at an advanced stage. *Trypanosoma brucei rhodesiense* (*T.b. rhodesiense*) is found in southern and east Africa. It causes acute infection that emerges after a few weeks. It is more virulent than the other strain and develops more rapidly, which means that it is more quickly detected clinically.

Other sub-species of the parasite cause animal trypanosomiasis, which are pathogenic to animals and are often different from those that cause the disease in humans. Animals can carry parasites, especially *T.b. rhodesiense*; domestic and wild animals are a major reservoir. They can also be infected with *T.b. gambiense*, though the precise role of this reservoir is not well known. The two human and animal forms of the disease remain a major obstacle to the development of rural regions of sub-Saharan Africa: human loss, decimation of cattle and abandonment of fertile land where the disease is rife.

There have been three severe epidemics in Africa over the last century: one between 1896 and 1906, mostly in Uganda and the Congo Basin, one in 1920 in several African countries, and one that began in 1970 and is still in progress. The 1920 epidemic was arrested due to mobile teams systematically screening millions of people at risk. The disease had practically disappeared between 1960 and 1965. After that success, screening and effective surveillance were relaxed, and the disease has reappeared in endemic form in several foci over the last thirty years.

Sleeping sickness threatens over 60 million people in 36 countries of sub-Saharan Africa. Only 3 to 4 million people at risk are under surveillance, with regular examination or access to a health centre that can provide screening. Detection of the disease calls for major human and material resources, such as well-equipped health centers and qualified staff. Because such resources are lacking, most people with sleeping sickness die before they can ever be diagnosed. Almost 45,000 cases were reported in 1999, but the World Health Organization (WHO) estimates that the number of people affected is ten times greater. The 45,000 case figure shows not the true situation but rather the lack of screening in many foci. The real number of cases seems to be between 300,000 and 500,000. Reported cases in recent years are from countries where surveillance coverage is no more than 5%.

In certain villages of many provinces of Angola, the Democratic Republic of Congo and southern Sudan, the prevalence is between 20% and 50%. Sleeping sickness has become the first or second greatest cause of mortality, ahead of HIV/AIDS, in those provinces.

Countries are placed in four categories in terms of prevalence. In each country the spatial distribution of the disease is very diverse; it is found in foci and micro-foci. Countries where there is an epidemic of the disease, in terms of very high cumulated prevalence and high transmission: Angola, Democratic Republic of Congo and Sudan. Highly endemic countries, where prevalence is moderate but increase is certain: Cameroon, Central African Republic, Chad, Congo, Côte d'Ivoire, Guinea, Mozambique, Uganda and United Republic of Tanzania. Countries where the endemic level is low: Benin, Burkina Faso, Equatorial Guinea, Gabon, Kenya, Mali, Togo and Zambia. Countries whose present status is not clear: Botswana, Burundi, Ethiopia, Liberia, Namibia, Nigeria, Rwanda, Senegal and Sierra-Leone.

The disease is transmitted with the bite of the tsetse fly. At first the trypanosomes multiply in the blood, and that process can last for years with *T.b. gambiense*. Mother-to-child infection: the trypanosome can cross the placenta and infect the fetus, causing abortion and perinatal death. Accidental infections can occur in laboratories, for example, through the handling of blood of an infected person, although this is fairly rare. The early phase entails bouts of fever, headaches, pains in the joints and itching. The second, known as the neurological phase, begins when the parasite crosses the blood-brain barrier and infests the central nervous system. This is when the characteristic signs and symptoms of the disease appear: confusion, sensory disturbances and poor coordination. Disturbance of the sleep cycle, which gives the disease its name, is the most important feature. Without treatment, the disease is fatal. If the patient does not receive treatment before the onset of the second phase, neurological damage is irreversible even after treatment.

There are three stages to case management: Screening is the initial sorting of people who might be infected. This involves checking for clinical signs or the use of serological tests. Diagnosis shows whether the parasite is present. The only sign, one that has been known for centuries, is swollen cervical glands. Phase diagnosis shows the state of progression of the disease. It entails examination of cerebro-spinal fluid obtained by lumbar puncture and is used to determine the course of treatment. The long, asymptomatic first phase of *T.b. gambiense* sleeping sickness is one of the factors that makes treatment difficult. Diagnosis must be made as early as possible in order to preclude the onset of irreversible neurological disorders and prevent transmission. Case detection is difficult and requires major human, technical and material resources. Since the disease is rife in rural areas among poor people with little access to health facilities, this problem is all the more difficult.

If the disease is diagnosed early, the chances of cure are high, but early diagnosis of the disease, which would guarantee low-risk treatment on an outpatient basis, can rarely be achieved. The type of treatment depends on the phase of the disease: initial or neurological. Success in the latter phase depends on having a drug that can cross the blood-brain barrier to reach the parasite. Four drugs have been used until now. However drugs are old, difficult to administer in poor conditions and by no means always successful.

Malaria is a life-threatening parasitic disease transmitted by mosquitoes. Today approximately 40% of the world's population—mostly those living in the world's poorest countries—is at risk of malaria. The disease was once more widespread but it was successfully eliminated from many countries with temperate climates during the mid 20th century. Today malaria is found throughout the tropical and sub-tropical regions of the world and causes more than 300 million acute illnesses and at least one million deaths annually. Ninety per cent of deaths due to malaria occur in Africa, south of the Sahara—mostly among young children. Malaria kills an African child every 30 seconds. Many children who survive an episode of severe malaria may suffer from learning impairments or brain damage. Pregnant women and their unborn children are also particularly vulnerable to malaria, which is a major cause of perinatal mortality, low birth weight and maternal anemia.

Malaria parasites have become resistant to one drug after another and many insecticides are no longer useful against the mosquitoes which transmit the disease. Years of vaccine research have produced few hopeful candidates.

Because of the general lack of effective, inexpensive chemotherapeutic agents for treating parasitic protozoal diseases that occur in the developing world, new chemotherapeutic agents are needed. For example, it is estimated that approximately 1.5–2 million new cases of leishmaniasis occur each year due to infection by various *Leishmania* species.[1] Pentavalent antimonial drugs are the first line treatment for leishmaniasis in most affected areas, with amphotericin B and pentamidine being used as alternatives.[2] These agents must be administered by injection over several days to weeks, increasing the cost and inconvenience of the drugs. Resistance to antimonials has become a severe problem,[3] and treatment with amphotericin B and pentamidine is frequently complicated by the occurrence of toxic side effects.[2] Clearly, improved chemotherapeutics are needed against this disease, as well as the other parasitic diseases.

SUMMARY OF THE INVENTION

The present invention provides a new class of dinitroaniline sulfonamide pharmaceutical compounds useful for the treatment of diseases caused by parasitic protozoa. The invention further provides pharmaceutical compositions made from the compounds of the present invention. The invention further provides methods of treating subjects having diseases caused by parasitic protozoa by administering a therapeutically effective amount of a compound of the present invention, or a pharmaceutically acceptable salt or ester thereof, to the subject. The compounds and methods of the present invention are particularly useful in the treatment of subjects having leishmanaisis.

The dinitroaniline compounds of the present invention are those of Formula I:

I wherein $R_1$ and $R_2$ are selected from the group consisting of H and $C_1$–$C_{10}$ alkyl, provided that $R_1$ and $R_2$ are not both n-propyl; or $R_1$ and $R_2$ can form a 5 or 6 membered ring containing C, N, and O, such as morpholino or pyrrolindino. Preferably $R_1$ and $R_2$ are methyl, ethyl, propyl, or butyl. $R_3$ is a sulfonamide, which is optionally substituted with $C_1$–$C_{10}$ alkyl, aryl, alkylaryl, alkoxyaryl, or haloaryl.

A subclass of compounds of special interest are those of Formula II:

II wherein $R_4$ and $R_5$ are the same and selected from the group consisting of butyl, pentyl, and hexyl, or $R_4$ and $R_5$ form a pyrrolidine ring; and $R_6$ is selected from the group consisting of H, $C_1$–$C_{10}$ alkyl, aryl, alkylaryl, alkoxyaryl, and haloaryl.

Another subclass of interest are the compounds of formula III:

III wherein n is 1, 2, 3, or 4 and Y is selected from the group consisting of $NH_2$, $C_6NH$, $C_6H_4(OCH_3)NH$, $C_6H_4(CH_3)NH$, $C_6H_4ClNH$, provided that when n=2 Y is not $NH_2$. Preferred compounds of formula III include: 4(dibutylamino)-3,5-dinitrobenzenesulfonamide; N1-Phenyl-3,5dinitro-N4,N4-di-n-propylsulfonilamide; N1-(3-Methoxy)phenyl-3,5-dinitro-N4,N4-di-n-propylsulfonilamide; N1-(3-Methyl)phenyl-3,5-dinitro-N4,N4-di-n-propylsulfonilamide; N1-Phenyl-3,5-dinitro-N4,N4-di-n-ethylsulfonilamide; and N1-Phenyl-3,5-dinitro-N4,N4-di-n-butylsulfonilamide. Especially preferred compounds for the treatment of *L. donovani* are: N1-Phenyl-3,5-dinitro-N4,N4-di-n-propylsulfonilamide; N1-(3-Methoxy)phenyl-3,5-dinitro-N4,N4-di-n-propylsulfonilamide; and N1-Phenyl-3,5-dinitro-N4,N4-di-n-butylsulfonilamide. Especially preferred compounds for the treatment of *T. b. brucei* are: N1-Phenyl-3,5-dinitro-N4,N4-di-n-propylsulfonilamide; N1-(3-Methoxy)phenyl-3,5-dinitro-N4,N4-di-ni-propylsulfonilamide; N1-(3-Methyl)phenyl-3,5-dinitro-N4,N4-di-n-propylsulfonilamide; N1-Phenyl-3,5-dinitro-N4,N4-di-n-ethylsulfonilamide; and N1-Phenyl-3,5-dinitro-N4,N4-di-n-butylsulfonilamide.

It is preferred that the compounds of Formulae I, II, and III bind to the tubulin of the parasitic protozoa. It is further preferred that the compounds of Formulae I, II, and III preferentially bind to the tubulin of parasitic protozoa rather than mammalian tubulin. In accordance with the present invention, it is especially preferred that the compounds of Formulae I, II, and III bind to the tubulin of parasitic protozoa with greater specificity than oryzalin.

The present invention also relates to pharmaceutical compositions containing the antileishmanial dinitroaniline sulfonamide compounds of the current invention in a pharmaceutically acceptable carrier. The present invention further relates to pharmaceutically acceptable derivatives of the antileishmanial dinitroaniline sulfonamide compounds.

The present invention further relates to methods of using the compounds to treat diseases caused by parasitic protozoa, specifically leishmaniasis, including visceral leishmaniasis, mucocutaneous leishmaniasis, and cutaneous leishmaniasis, caused by protozoa of the *Leishmania* genus, such as *Leishmania donovani*. The invention further relates to methods of treating other diseases caused by parasitic protozoa, including Chagas disease; human African trypanosomiasis, also known as African sleeping sickness; animal trypanosomiasis; and malaria. These diseases are caused by the protozoa *Trypanosoma cruzi Trypanosoma brucie gambiense, Trypanosoma brucie rhodesiense, Plasmodium falciparum, Plasmodium vivax, Plasmodium ovali*, and *Plasmodium malariae*.

DETAILED DESCRIPTION OF THE INVENTION

Figure 1:
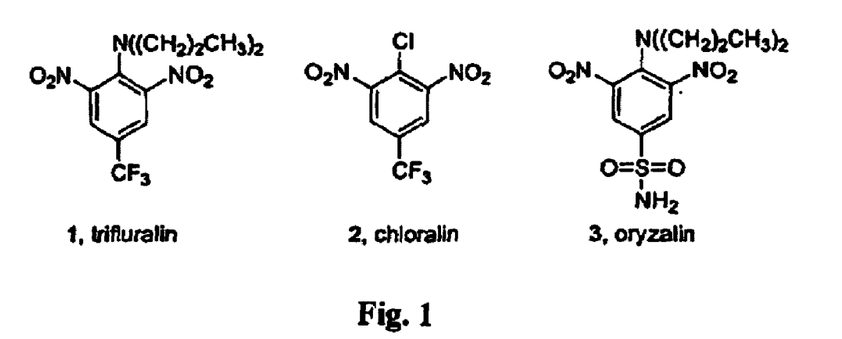
FIG. 1 Shows the structures of trifluralin, chloralin, and oryzalin.

In the early 1990, reports that the commercial herbicide trifluralin (1, FIG. 1), a dinitroaniline that binds to plant but not animal tubulin,[4] possessed selective antileishmanial activity were therefore cause for optimism. Trifluralin inhibited the proliferation of *Leishmania* amastigotes in macrophages, and radiolabeled trifluralin was shown to bind better to partially purified leishmanial tubulin than to rat brain tubulin.[5] Trifluralin has also been reported to possess activity in animal models of leishmaniasis.[6] Unfortunately, the story of trifluralin's antiparasitic potential has become more confusing with time. The synthetic precursor of trifluralin, chloralin (2, FIG. 1), is often present as an impurity in commercial trifluralin preparations, and chloralin was much more toxic to *Leishmania* in vitro than trifluralin.[7] We subsequently purified leishmanial tubulin in our own laboratory and found that chloralin, in addition to being a much more effective in vitro antileishmanial agent than trifluralin, was an inhibitor of leishmanial tubulin polymerization while trifluralin was not.[8] Other reports describing the effects of trifluralin and related compounds on protozoan parasites have appeared,[9,10] but the effects of these compounds on parasite tubulin were not examined Trifluralin also presents serious technical problems due to its low solubility.[4] It is therefore difficult to determine whether 1 is a useful antileishmanial lead compound that targets protozoal tubulin from the studies described above.

The antimitotic effects of the related dinitroaniline herbicide oryzalin (3, FIG. 1) on *Leishmania* have also been described.[11] Oryzalin, which contains a sulfonamide group in place of the trifluoromethyl functionality present in trifluralin, possesses approximately tenfold greater aqueous solubility than trifluralin.[4] We obtained a commercial sample of oryzalin and found that it did indeed inhibit the assembly of purified leishmanial tubulin and was moderately toxic to *Leishmania* parasites in vitro (K. Werbovetz, unpublished results). On the basis of this positive result, we decided to employ oryzalin as a lead compound to explore the structure-activity relationship of dinitroanilines against leishmanial tubulin and against *Leishmania* parasites in vitro.

The present invention provides compounds useful for treating diseases caused by parasitic protozoa specifically *Leishmania donovani*, and also including *Trypanosoma cruzi, Trypanosoma brucie gambiense, Trypanosoma brucie rhodesiense, Plasmodium falciparum, Plasmodium vivax, Plasmodium ovali*, and *Plasmodium malariae*. The methods of the present invention comprise treating a subject affected with a diseased caused by a parasitic protozoan with a therapeutically effective amount of a compound of the present invention or a derivative or pharmaceutically acceptable salt or ester thereof.

SYNTHESIS AND EXAMPLES

Figure 3:
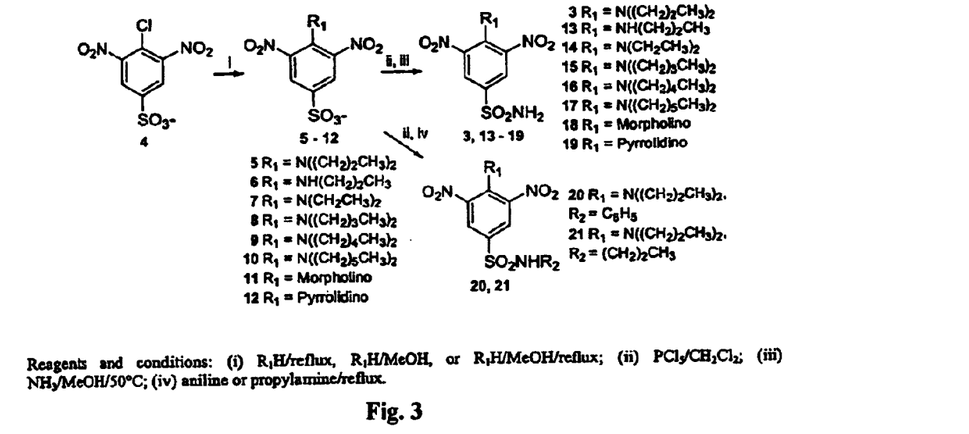
FIG. 3 shows the reaction scheme for preparation of compounds 3 and 13–21.

Synthesis of Compounds 13–21 We first synthesized oryzalin and thirteen new dinitroaniline compounds that differ from 3 in one region of the molecule. Target sulfonamides 3 and 13–21 were prepared as shown in Scheme 1. The key intermediate 4-chloro-3,5-dinitrobenzenesulfonic acid 4[12] was converted to amines 5–12 by heating 4 to reflux with the corresponding amine (for dipropyl 5, propyl 6 and diethylamine 7 derivatives) or by treating 4 with a methanol solution containing the desired amine (for dibutyl 8, dipentyl 9, and dihexylamine 10 derivatives). The morpholino (11) and pyrrolidino (12) derivatives were prepared by stifling compound 4 in a methanolic solution containing either morpholine or pyrrolidine. Sulfonic acids 5–12 were then converted to the corresponding sulfonyl chloride derivatives (which were not isolated due to their unstable nature) by $PCl_5/CH_2Cl_2$ treatment. The sulfonyl chlorides were then transformed to sulfonamide derivatives by treatment with either ammonia in MeOH (3, 13–19), aniline (20), or propylamine (21).

Figure 4:
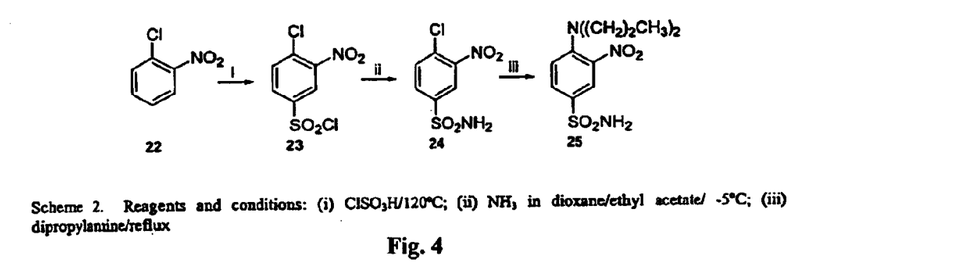
FIG. 4 shows the reaction scheme for preparation of compound 25.

Synthesis of Compound 25 Mononitro derivative 25 was prepared as indicated in Scheme 2. 1-Chloro-2-nitrobenzene 22 was converted to 23 by heating at 120° C. in chlorosulfonic acid, which was then transformed to the sulfonamide 24 at −5° C. by reaction with ammonia in dioxane/ethyl acetate. Sulfonamide 24 was then converted to 25 by treatment with dipropylamine at reflux.

Figure 5:
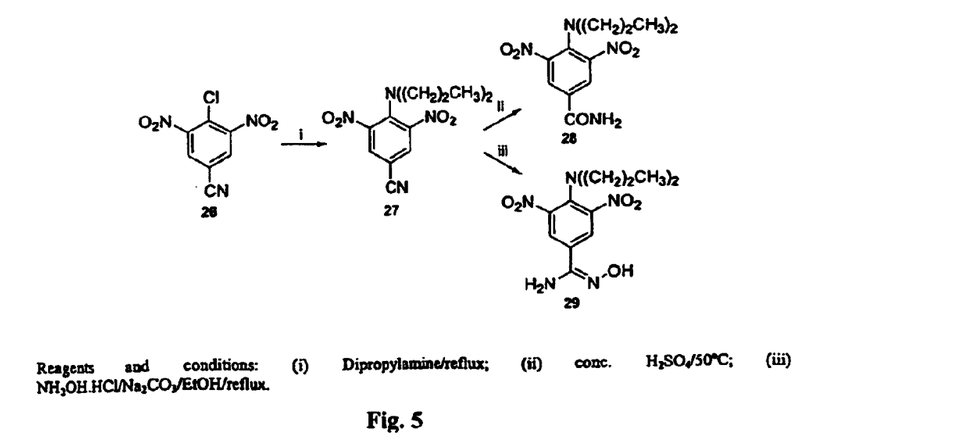
FIG. 5 shows the reaction scheme for preparation of compounds 27–29.

Synthesis of Compounds 27–29 Cyano, amide and amidoxime compounds 27–29 were prepared according to Scheme 3. Commercially available 4-chloro-3,5-dinitrobenzonitrile 26 was converted to the corresponding dipropylamine derivative 27 by a modified Ullmann condensation using dipropylamine under reflux conditions to achieve nearly quantitative yield. Benzonitrile 27 was converted to amide 28 by hydrolysis with conc. $H_2SO_4$ at 50° C. The amidoxime derivative 29 was prepared by heating 27 with $NH_2OH.HCl/Na_2CO_3$ in a solution of ethanol/water at reflux[13]. Target compounds 3, 13–20, 25, and 27–29 were purified by silica gel column chromatography and crystallization. These molecules possessed satisfactory $^1$H NMR and mass spectra and did not contain detectable traces of electrophilic precursors.

Example 1

Inhibition of Leishmanial Tubulin Assembly for Compounds 3, 13–21, 25, 27–29

With the desired compounds in hand, we then examined oryzalin and several new dinitroaniline compounds for their ability to block the growth of *Leishmania donovani* parasites and to inhibit the assembly of purified leishmanial tubulin by methods described previously in Havens, C.; Bryant, N.; Asher, L.; Lamoreaux, L.; Perfetto, S.; Brendle, J.; Werbovetz, K., "Cellular effects of leishmanial tubulin inhibitors on *L. donovani*," Mol. Biochem. Parasitol. 2000, 110, 223–236, incorporated herein by reference.[14]

Briefly, the tubulin assembly assays are performed as follows. Assembly reactions were performed in 96-well half-area microplates (Costar) in a final volume of 50 ∝L. For both leishmanial and brain tubulin, reactions contained final concentrations of 1.5 mg/mL (15 ∝M) tubulin, 0.1 mM PIPES (pH 6.9), 1 mM EGTA, 1 mM $MgCl_2$, 10% (v/v) DMSO, and 1 mM GTP with and without compounds of interest Components of the reaction mixtures were added to the microplate on ice, then assembly was initiated by the simultaneous addition of a GTP solution to all sample wells with a multichannel pipet. The change in turbidity was measured at 351 nm using the SpectraMax Plus microplate reader immediately after GTP addition at 30° C. (for leishmanial tubulin) or 37° C. (for brain tubulin). To ensure maximal solubility of GB-II-5 at a concentration of 40 ∝M, compounds were added to reactions containing brain tubulin in 5 ∝L volumes containing 100% DMSO, and assembly was initiated by adding 10 ∝L of 5 mM GTP in water. The assembly of leishmanial tubulin occurred too rapidly for accurate measurement under the conditions described for brain tubulin. Since lower concentrations of 20 affect leishmanial tubulin and solubility was thus not as much of a concern, compounds were added to reactions containing parasite tubulin in 5 ∝L volumes containing 50% DMSO, then assembly was initiated by adding 10 ∝L of 5 mM GTP in 25% DMSO.

Moderate antiparasitic and antitublin activity was observed with 3; mid-micromolar concentrations of this compound inhibited parasite growth and 20 µM concentrations of 3 inhibited the assembly of leishmanial tubulin by about 50% (Table 1). Compound 13, in which the dipropyl substitution present at the N4 position of the sulfanilamide core of 3 is replaced by a propyl group, displays similar antiparasitic activity and activity against the target protein compared to 3. When the alkyl chain length was shortened from three to two carbons in compound 14, antiparasitic activity and potency against the target protein were again comparable with 3. Interestingly, an increase in the length of the dialkylamine chain present in 3 dramatically improved antileishmanial activity. Compounds 15–17 were 2.5- to 5.5-fold more active against the promastigote stage of the parasite and 3.6- to 8.1-fold more active against *L. donovani* axenic amastigotes than 3, while 15 and 16 possess superior activity compared to 3 against the putative target protein. Restricting the conformation of the alkylamine chain, as in the morpholino compound 18 and the pyrrolidino compound 19, decreased activity against *Leishmania* parasites. A difference between 18 and 19 was noted in antitubulin activity, as the pyrrolidino compound 19 was similar to oryzalin against tubulin but the morpholino compound 18 was inactive against the protein.

TABLE 1

Activity of Oryzalin and New dinitroaniline compounds 13–29 Against *L. donovani* and Against Leishmanial Tubulin in vitro

| Compound | $IC_{50}$ vs. *L. donovani* promastigotes (µM)[a] | $IC_{50}$ vs. *L. donovani* amastigotes (µM)[a] | % Inhibition of Leishmanial Tubulin Assembly at 20 µM Compound[b] |
|---|---|---|---|
| Pentamidine | 1.61 ± 0.22 | 2.00 ± 0.06 | $NT^c$ |
| 3 (oryzalin) | 44.1 ± 9.2 | 72.5 ± 23.9 | 54 ± 14 |
| 13 | 67.0 ± 18.4 | NT | 43 ± 19 |
| 14 | 69.3 ± 23.0 | NT | 58 ± 22 |
| 15 | 17.8 ± 2.6 | 20.1 ± 0.2 | 89 ± 3 |
| 16 | 8.02 ± 0.42 | 9.0 ± 0.7 | 95 ± 5 |
| 17 | 12.2 ± 0.0 | 11.7 ± 0.7 | 48 ± 19 |
| 18 | >100 | NT | 21 ± 1 |
| 19 | 97.1 ± 53.0 | NT | 57 ± 18 |
| 20 | 14.7 ± 1.0 | 5.41 ± 0.89 | 108 ± 7 |
| 21 | 56.0 ± 2.3 | 56.9 ± 3.4 | 97 ± 1 |
| 25 | 89.8 ± 15.3 | NT | 19 ± 29 |
| 27 | >100 | NT | 25 ± 17 |
| 28 | 76.4 ± 20.0 | NT | 34 ± 12 |
| 29 | >100 | NT | 35 ± 7 |

[a]Mean ± standard deviation of at least two independent measurements
[b]Mean ± standard deviation of at least one duplicate measurement. The standard deviation of the control samples in these experiments was 27.6%
[c]NT—Not tested Another striking result was obtained with compounds 20 and 21, both substituted at the N1 position of the sulfanilamide core, in that these two compounds are much more potent inhibitors of leishmanial tubulin assembly than 3. Compound 20 is 3.0-fold more active against promastigotes and 13.4-fold more active against amastigotes than oryzalin 3, approaching the in vitro antiparasitic activity of the clinical antileishmanial agent pentamidine against the form of the parasite present in the mammalian host. Despite its improved activity against leishmanial tubulin, compound 21 is similar to 3 in antiparasitic activity. Other substitutions diminished the activity of the compounds. Removal of a single nitro group, as in 25, decreases the potency against cultured parasites and leishmanial tubulin. Replacement of the sulfonamide group with a cyano group, an amide functionality, or an amidoxime group as in 27–29 diminishes activity against *L. donovani* and leishmanial tubulin as well.

Our study clearly demonstrates that the pure dinitroanilines possess antileishmanial and antitubulin activity. While other reports showed that several different dinitroaniline compounds possessed antiparasitic activity,[9,15] evidence linking dinitroanilines with tubulin inhibition in parasites was less clear. In addition to chloralin 2, other small aromatic electrophiles are known to inhibit tubulin assembly in general[16,17] and leishmanial tubulin assembly in particular.[14] This report shows that several non-electrophilic nitroaniline compounds display potent effects against *Leishmania* parasites and against purified leishmanial tubulin, renewing hopes that such compounds could be leads for the discovery of new antiparasitic agents.

It is also clear that several synthetic, non-electrophilic dinitroaniline compounds are superior to 3 in their activity against leishmanial tubulin and cultured *Leishmania* parasites. Compounds 15–17 and 20 are significantly more potent against parasites than lead compound 3, with 20 being 13.4-fold more active than 3 against amastigote-stage *L. donovani*, and 15, 16, 20 and 21 are more potent than 3 in blocking leishmanial tubulin assembly. These data are consistent with the hypothesis that tubulin is the target of the dinitroanilines in *Leishmania*. Although an exact correlation was not observed between antiparasitic activity and the inhibition of leishmanial tubulin assembly, all of the compounds that are superior to oryzalin in antiparasitic activity are at least as potent as 3 in blocking parasite tubulin assembly in vitro. Thus inhibition of leishmanial tubulin polymerization appears to be a necessary but not sufficient property for members of this class of compounds to possess strong antileishmanial activity. An important factor that may help explain the lack of a direct correlation between antitubulin and antileishmanial activity of these compounds is penetration of the molecules into the parasite. Compounds 15–17 have longer alkyl chains than 3 and would thus be expected to be more hydrophobic than the parent compound, facilitating passage of compounds 15–17 across the parasite cell membrane. The difference in activity between 20 and 21 is harder to rationalize. Although both compounds are more potent inhibitors of leishmanial tubulin assembly than oryzalin, N1-phenyl sulfanilamide 20 is much more effective than 3 at blocking parasite growth, while N1-alkyl sulfanilamide 21 and 3 possess similar antiparasitic activity. Poor accumulation of 21 within the parasite may also explain these data.

Example 2

Cellular effects of the new dinitroaniline compounds on *Leishmania* We have verified that our new agents act through a microtubule mechanism in the parasites with the aid of flow cytometry and fluorescence microscopy.

Flow cytometry and fluorescence cell sorting. Parasites or J774 macrophages were incubated in T25 flasks (3–5 mL final volume) in the appropriate media described earlier for 24–48 h. Cultures contained 1% DMSO (v/v) in the presence or absence of test compounds. Cells were counted using a hemacytometer, then were centrifuged (1000×·g for parasites, 200×·g for macrophages) at 4° C. for 10 min (parasites) or 5 min (macrophages). Cells were resuspended in 150 µL of PBS (0.01 M phosphate, 0.137 M NaCl, and 2.7 mM KCl), then 350 µL of ice-cold methanol was added and the samples were fixed at −20° C. for 2–3 h. Cells were centrifuged as before and resuspended in PBS containing 0.1% TX-100, 5 µg/mL RNase A, and 10 µg/mL propidium iodide for 20–30 min. Centrifugation was repeated, then cells were resuspended in PBS to a final concentration of $5 \times 10^{5-106}$/mL and stored at 4° C. until analysis. Fluorescence cell sorting was conducted on a Beckman Coulter Elite flow cytometer.

Fluorescence microscopy. *L. donovani* promastigotes were incubated with or without test compounds for two days and centrifuged as described above. Parasites were resuspended in PBS at a concentration of $2 \times 10^7$ cells/mL, then $10^6$ parasites were applied to a microscope slide previously coated with 0.1 mg/mL poly-L-lysine. Parasites were allowed to adhere for 10 min, then the cells were fixed in methanol for 5 min, rinsed with PBS, then placed in 0.1% TX-100 in PBS for 5 min. Slides were then washed with PBS, and were incubated with a 1:100–1:1000 dilution of a FITC-conjugated anti α-tubulin antibody (clone DM 1A) for 1 h at room temperature. After washing the slides 3×· with PBS for 5 min each, 4',6-diamidino-2-phenylindole (DAPI) was applied to slides at a concentration of 10 µg/mL. Slides were washed again in PBS, then coverslips were mounted using Vectashield (Vector Laboratories, Burlingame, Calif.) in preparation for fluorescence microscopy using a Nikon Labophot-2 microscope equipped with a Nikon FX-35DX camera.

Figure 2:
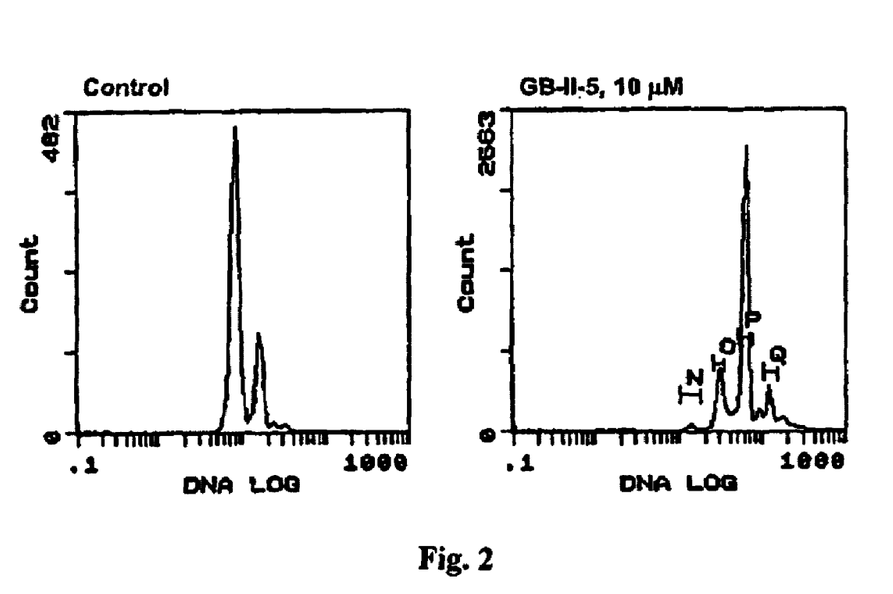
FIG. 2 is an analysis of DNA content in *L. donovani* by treated with compound 20 by flow cytometry. After 48 h treatments with 1% DMSO (Control) and 10 µM compound 20, parasites were fixed, stained with propidium iodide, and analyzed by flow cytometry.

Flow cytometry studies indicated that a 48 hour treatment of *L. donovani* promastigotes with 10 µM compound 15 caused parasites to accumulate in the $G_2M$ phase of the cell cycle, consistent with an effect on microtubules. Compound 15 at 10 µM was more potent in this flow cytometry assay than 50 µM concentrations of oryzalin. Even more dramatic effects were observed with compound 20, as treatment of promastigotes with 10 µM concentrations of this compound for 48 hours caused the appearance of parasites containing approximately 4×, 8×, and 16× more DNA than those observed in the $G_1$ phase of control samples (FIG. 2, note log scale). In this experiment, parasites in control cultures doubled approximately three times over the course of 48 hours, while compound 20-treated parasites remained at the same cell density. These results suggest that the compound 20-treated parasites failed mitosis after S-phase due to microtubule inhibition, but then continued through the cell cycle only to fail mitosis on one, two, or three additional occasions. Brightfield microscopy revealed aberrant forms that resembled cultures treated with the potent antimitotic natural product ansamitocin P3, and DAPI staining of these cultures showed that these parasites frequently contained multiple kinetoplasts as we observed previously in promastigotes treated with other known antimitotics.[14]

Example 3

Selectivity of the new dinitroaniline compounds. Since we are ultimately interested in developing antiparasitic agents that will be nontoxic to the host, selectivity is a critical parameter regarding these compounds. We have determined the selectivity of our compounds by using tubulin fluorescence quenching experiments.

Measurement of dissociation constants by fluorescence quenching. Binding of dinitroanilines to tubulin was measured by the resulting quenching of intrinsic tubulin tryptophan fluorescence, a method that has proved useful in protein binding studies of many compounds (23). The strong 300–350 nm absorbance of these compounds makes them good acceptors of resonance energy transfer from the photoexcited tryptophan residues, resulting in reduction of tryptophan fluorescence. Samples of tubulin with increasing concentrations of test compound were excited at 290 nm, and tryptophan fluorescence measured between 310 and 340 nm. Spectra were recorded using an ISS PC1 photon counting spectrofluorometer (ISS, Champaign, Ill.) with excitation and emission slits of 2 and 1 mm, respectively. Sample fluorescence was corrected for the small photobleaching by measuring a tubulin sample with additions of DMSO. Inner filter effects were corrected using a sample of N-acetyltryptophanamide, and additions of the test compound. The corrected fluorescence decrements as a function of test compound concentration were fitted to a single site binding model using the nonlinear fitting routines of Prism software (Graph Pad Software, San Diego, Calif.).

The results confirm our earlier conclusions that several of our new dinitroaniline compounds are better ligands for leishmanial tubulin than the lead compound (Table 2). These data are also in agreement with results indicating that oryzalin is a mediocre ligand for leishmanial tubulin, and provide the first quantitative measure of the selectivity of oryzalin for this protein. With the exception of compound 15, all of our compounds are more selective for leishmanial tubulin than mammalian tubulin, and the N1-substituted compounds, compound 20 and compound 21 are more selective than oryzalin for leishmanial tubulin.

TABLE 2

Dissociation Constants for New dinitroaniline compounds Against Leishmanial and Rat Brain Tubulin

| Compound | $K_d$ (μM) vs. Leishmanial Tubulin | $K_d$ (μM) vs. Brain Tubulin | Selectivity Index |
|---|---|---|---|
| Oryzalin, 3 | 170 | 24 | 7.1 |
| 20 | 57 | 5 | 11.4 |
| 21 | (770)* | 29 | 26.6 |
| 15 | 19 | 21 | 0.9 |
| 16 | 54 | 12 | 4.5 |
| 17 | 39 | 8 | 4.9 |
| ColchAC | 5 | (1300) | 0.004 |

Additional compounds were prepared as follows:

TABLE 3

Additional Compounds

| Compound | n | Y |
|---|---|---|
| 3 (oryzalin) | 2 | NH$_2$ |
| 15, above | 3 | NH$_2$ |
| 20, above | 2 | (phenyl)-NH |
| 30 | 2 | H$_3$CO-(phenyl)-NH (3-position) |
| 31 | 1 | (phenyl)-NH |
| 32 | 3 | (phenyl)-NH |

Comparative Examples

| 33 | 2 | NHCH$_3$ |
| 34 | 2 | N(CH$_3$)$_2$ |
| 35 | 2 | NHCH$_2$CH$_3$ |
| 36 | 2 | N(CH$_2$CH$_3$)$_2$ |
| 37 | 2 | NH(CH$_2$)$_2$CH$_3$ |
| 38 | 2 | NHCH(CH$_3$)$_2$ |
| 39 | 2 | H$_3$CO-(phenyl)-NH (4-position) |

TABLE 3-continued

Additional Compounds

| Compound | n | Y |
|---|---|---|
| 40 | 2 | H$_3$C-(phenyl)-NH (4-position) |
| 41 | 2 | Cl-(phenyl)-NH (4-position) |
| 42 | 2 | H$_3$C-(phenyl)-NH (3-position) |
| 43 | 2 | Cl-(phenyl)-NH (3-position) |
| 44 | 2 | 3,4-diCl-(phenyl)-NH |
| 45 | 2 | 3,5-diCl-(phenyl)-NH |
| 46 | 2 | (2-pyridyl)-NH |

TABLE 3-continued

Additional Compounds

| Compound | n | Y |
|---|---|---|

3-22

Example 4

N1-Phenyl-3,5-dinitro-N4,N4-di-n-propylsulfonilamide (20) was synthesized by the reaction of the sulfonyl chloride and 547 μL (6 mmol) of aniline in 20 mL pyridine. The product was isolated by chromatography (hexane/EtOAc (3:1)) and crystallized by dichloromethane/hexane to afford a yellow crystalline solid; yield 342 mg, 81%, mp=120° C.; $^1$H NMR$^3$ $^{13}$C NMR (DMSO-d$_6$)$^3$. MS (FAB) m/z Calcd for $C_{18}H_{22}H_4O_6S$ (M+Na)$^+$445.1158, Measured (M+Na)$^+$ 445.1164. Anal. ($C_{18}H_{22}N_4O_6S$) C, H, N.

Example 5

N1-(3-Methoxy)phenyl-3,5-dinitro-N4,N4-di-n-propyl-sulfonilamide (30) was synthesized by the reaction of the sulfonyl chloride and 369 mg (3 mmol) of 4-methoxyaniline in 20 mL pyridine. The product was isolated by chromatography (hexane/EtOAc (6:1)) and crystallized using dichloromethane/hexane to obtain a yellow crystalline solid; yield 14.5%; mp.=133° C.; $^1$H NMR (CDCl$_3$) δ 0.86 (t, 6H, J=7.33 Hz), 1.58 (m, 4H), 2.93 (t, 4H, J=7.40 Hz), 3.78 (s, 3H), 6.49 (bs, 1H), 6.75 (m, 3H), 7.21 (m, 1H), 8.12 (s, 2H); $^{13}$C NMR (CDCl$_3$) δ 11.00, 20.55, 53.89, 55.39, 107.45, 111.70, 113.62, 128.73, 128.89, 130.38, 136.51, 141.72, 144.26, 160.46. MS m/z 451.1 (M−H)$^−$. Anal. Calcd. For $C_{19}H_{24}N_4O_7S$ C, H, N.

Example 6

N1-Phenyl-3,5-dinitro-N4,N4-di-n-ethylsulfonilamide (31). The sulfonyl chloride derivative was prepared from the sulfonic acid and PCl$_5$. It was then treated with 547 μL (6 mmol) of aniline in 20 mL pyridine. The product was isolated by chromatography (hexane/EtOAc (6:1)) and crystallized using dichloromethane/hexane to afford a yellow crystalline solid; yield 262 mg, 67%; mp=157° C. $^1$H NMR (DMSO-d$_6$) δ 0.99 (t, 6H, J=7.00 Hz), 2.99 (q, 4H, J=7.00 Hz), 7.17 (m, 5H), 8.28 (s, 2H), 10.45 (bs, 1H); $^{13}$C NMR (DMSO-d$_6$) δ 12.54, 45.60, 120.82, 124.95, 127.92, 129.43, 130.69, 136.73, 140.63, 144.96. MS m/z 392.9 (M−H)$^−$. Anal. ($C_{16}H_{18}N_4O_6S$) C, H, N.

Example 7

N1-Phenyl-3,5-dinitro-N4,N4-di-n-butylsulfonilamide (32). The sulfonyl chloride derivative was prepared as before from the sulfonic acid and PCl$_5$. It was then treated with 547 μL (6 mmol) of aniline in 20 mL pyridine. The product was isolated by chromatography (hexane/EtOAc (6:1)) and crystallized by dichloromethane/hexane to afford a yellow crystalline solid. Yield 286 mg, 64%; mp=156° C. $^1$H NMR (CDCl$_3$) δ 0.87 (t, 6H, J=7.50 Hz), 1.28 (m, 4H), 1.55 (m, 4H), 2.96 (t, 4H, J=7.50 Hz), 6.57 (bs, 1H), 7.25 (m, 5H), 8.10 (s, 2H). $^{13}$C NMR (CDCl$_3$) δ 13.66, 19.85, 29.35, 52.07, 122.18, 126.52, 128.61, 129.09, 129.78, 135.24, 141.66, 144.42. m/z Calcd For $C_{20}H_{26}N_4O_6S$ (M−H)$^−$ 449.0. Anal. ($C_{20}H_{26}N_4O_6S$) C, H, N.

Comparative Example A

N1-Methyl-3,5-dinitro-N4,N4di-n-propylsulfonilamide (33) was synthesized by the reaction of the sulfonyl chloride and 10 mL of 2 M methylamine in THF. The product was isolated by chromatography using hexane/EtOAc 2:1 as eluent and crystallized using dichloromethane/hexane to obtain yellow crystals; yield 88 mg, 97%; mp=148° C.; $^1$H NMR (CDCl$_3$) δ 0.86 (t, 6H, J=7.25 Hz), 1.62 (m, 4H), 2.76 (d, 3H, J=5.25 Hz), 2.97 (m, 4H), 4.38 (bq, 1H), 8.25 (s, 2H); $^{13}$C NMR (CDCl$_3$) δ 11.06, 20.63, 29.31, 53.94, 128.47, 129.55, 141.48, 144.61. MS m/z 361.00 (M+H)$^+$. Anal. ($C_{13}H_{20}N_4O_6S$) C, H, N.

Comparative Example B

N1,M1-Dimethyl-3,5-dinitro-N4,N4-di-n-propylsulfonil-amide (34) was synthesized by the reaction of the sulfonyl chloride and 10 mL of 2 M dimethylamine in THF. The product was isolated by chromatography (hexane/EtOAc (2:1) and crystallized using dichloromethane/hexane to obtain yellow crystals; yield 85 mg, 91%; mp=138° C.; $^1$H NMR (CDCl$_3$) δ 0.89 (t, 6H, J=7.25 Hz), 1.63 (m, 4H), 2.81 (s, 6H), 2.98 (m, 4H), 8.15 (s, 2H); $^{13}$C NMR (CDCl$_3$) δ 6 11.05, 20.62, 37.76, 53.89, 126.88, 128.64, 141.47, 144.65. MS m/z 397.00 (M+Na)$^+$. Anal. ($C_{14}H_{22}N_4O_6S$) C, H, N.

Comparative Example C

N1-Ethyl-3,5-dinitro-N4,N4-di-n-propylsulfonilamide (35) was synthesized by the reaction of the sulfonyl chloride and 10 mL of 2 M ethylamine in THF. The product was isolated by chromatography (hexane:EtOAc=3:1) and crystallized using dichloromethane/hexane to obtain yellow crystals; yield 78 mg, 83%; mp=131° C.; $^1$H NMR (CDCl$_3$) δ 0.88 (t, 6H, J=7.25 Hz), 1.20 (t, 3H, J=7.25 Hz), 1.62 (m, 4H), 3.08 (m, 6H), 4.44 (bt, 1H), 8.24 (s, 2H); $^{13}$C NMR (CDCl$_3$) δ 11.06, 15.13, 20.63, 38.41, 53.94, 128.32, 130.64, 141.39, 144.61. MS m/z 372.9 (M−H)$^−$. Anal. ($C_{14}H_{22}N_4O_6S$) C, H, N.

Comparative Example D

N1,N1-Diethyl-3,5-dinitro-N4,N4-di-n-propylsulfonil-amide (36) was synthesized by the reaction of the sulfonyl chloride and 10 mL (0.79 mol) of diethylamine. The product was isolated by chromatography (hexane:EtOAc (6:1)) and crystallized using dichloromethane/hexane to obtain yellow crystals; yield 73 mg, 73%; mp=102° C.; $^1$H NMR (CDCl$_3$) δ 0.88 (m, 6H), 1.20 (t, 6H, J=7.25 Hz), 1.62 (m, 4H), 2.97 (m, 4H), 3.28 (q, 4H, J=7.00 Hz), 8.18 (s, 2H); $^{13}$C NMR (CDCl₃) δ 11.05, 14.27, 20.63, 42.38, 53.92, 128.03, 131.35, 141.07, 144.73. MS m/z 403.1 (M+H)⁺. Anal. ($C_{16}H_{26}N_4O_6S$) C, H, N.

Comparative Example E

N1-Propyl-3,5-dinitro-N4,N4-di-n-propylsulfonilamide (37) was synthesized by the reaction of the sulfonyl chloride and 10 mL (0.12 mol) of propylamine. The product was isolated by chromatography (hexane:EtOAc (3:1)) and crystallized using dichloromethane/hexane to obtain yellow crystals; yield 86 mg, 88%; mp=114° C.; ¹H NMR (DMSO-d₆) δ 0.82 (m, 9H), 1.55 (m, 6H), 2.97 (m, 6H), 7.88 (bs, 1H), 8.37 (s, 2H); ¹³C NMR (DMSO-d₆) δ 11.24, 11.38, 20.74, 22.77, 44.64, 53.71, 128.27, 132.28, 140.59, 145.11. MS m/z 389.3 (M+H)⁺. Anal. ($C_{15}H_{24}N_4O_6S$) C, H, N.

Comparative Example F

N1-Isopropyl-3,5-dinitro-N4,N4-di-n-propylsulfonilamide (38) was synthesized by the reaction of the sulfonyl chloride and 10 mL (0.12 mol) of isopropylamine. The product was isolated by chromatography (hexane/EtOAc (6:1)) and crystallized using dichloromethane/hexane to give a yellow crystalline solid; yield 77 mg, 79%; mp=150° C.; ¹H NMR (CDCl₃) δ 0.88 (t, 6H, J=7.25 Hz), 1.27 (d, 6H, J=7.25 Hz), 1.63 (m, 4H), 2.97 (m, 4H), 3.57 (m, 1H), 4.41 (bs, 1H), 8.25 (s, 2H); ¹³C NMR (CDCl₃) δ 11.11, 20.70, 23.85, 46.68, 54.07, 128.22, 131.99, 141.33, 144.71. MS m/z 389.0 (M+H)⁺. Anal. ($C_{15}H_{24}N_4O_6S$) C, H, N.

Comparative Example G

N1-(4-Methoxy)phenyl-3,5-dinitro-N4,N4-di-n-Propylsulfonilamide (39) was synthesized by the reaction of the sulfonyl chloride and 369 mg (3 mmol) of 4-methoxyaniline in 20 mL pyridine. The product was isolated by chromatography (hexane/EtOAc (6:1)) and crystallized using dichloromethane/hexane to obtain a yellow crystalline solid; yield 221 mg, 69%; mp=121° C.; ¹H NMR (CDCl₃) δ 0.86 (t, 6H, J=7.25 Hz), 1.61 (m, 4H), 2.91 (m, 4H), 3.79 (s, 3H), 6.58 (bs, 1H), 6.83 (dd, 2H, J=2.00, 7.00Hz), 7.30 (dd, 2H, J=2.00, 7.00 Hz), 8.04 (d, 2H, J=0.75 Hz); ¹³C NMR (CDCl₃) δ 11.08, 20.65, 53.99, 55.49, 114.85, 125.92, 127.42, 128.60, 129.31, 141.53, 144.40, 158.71. MS (FAB) m/z Calcd for $C_{19}H_{24}N_4O_7S$ (M+Na)⁺ 475.1263, Measured (M+Na)⁺ 475.1275. Anal. ($C_{19}H_{24}N_4O_7S$) C, H, N.

Comparative Example H

N1-(4Methyl)phenyl-3,5-dinitro-N4,N4-di-n-propylsulfonilamide (40) was synthesized by the reaction of the sulfonyl chloride and 321 mg (3 mmol) of 4-methylaniline in 20 mL pyridine. The product was isolated by chromatography (hexane/EtOAc (6:1)) and crystallized using dichloromethane/hexane to obtain yellow crystals; yield 338 mg, 77%; mp=107° C.; ¹H NMR (CDCl₃) δ 0.85 (t, 6H, J=7.25 Hz), 1.60 (m, 4H), 2.31 (s, 3H), 2.91 (t, 4H, J=7.75 Hz), 6.77 (bs, 1H), 7.10 (d, 2H, J=8.25 Hz), 7.20 (d, 2H, J=8.25 Hz), 8.10 (d, 2H, J=0.75 Hz)); ¹³C NMR (CDCl₃) δ 11.08, 20.65, 20.85, 53.99, 122.87, 128.61, 129.33, 130.27, 132.44, 136.76, 141.61, 144.39. MS (FAB) m/z Calcd for $C_{19}H_{24}N_4O_6S$ (M+Na)⁺459.1314, Measured (M+Na)⁺ 459.1316. Anal. ($C_{16}H_{24}N_4O_6S$) C, H, N.

Comparative Example I

N1-(4-Chloro)phenyl-3,5dinitro-N4,N4-di-n-propylsulfonilamide (41) was synthesized by the reaction of the sulfonyl chloride and 351 mg (3 mmol) of 4-chloroaniline in 20 mL pyridine. The product was isolated by chromatography (hexane/EtOAc (6:1)) and crystallized by dichloromethane/hexane to obtain yellow crystals; yield 258 mg, 58%; mp=130° C.; ¹H NMR (CDC₃) δ 0.86 (t, 6H, J=7.50 Hz), 1.61 (m, 4H), 2.94 (m, 4H), 6.95 (bs, 1H), 7.09 (d, 2H, J=7.25 Hz), 7.30 (d, 2H, J=7.25 Hz), 8.14 (d, 2H, J=0.15 Hz); ¹³C NMR (CDCl₃) δ 11.09, 20.65, 54.03, 123.37, 128.65, 128.77, 129.92, 132.21, 133.75, 141.85, 144.38. MS (FAB) m/z Calcd for $C_{18}H_{21}ClN_4O_6S$ (M+Na)⁺ 479.0768, Measured (M+Na)+ 479.0767. Anal. ($C_{18}H_{21}ClN_4O_6S$) C, H, N.

Comparative Example J

N1-(3-Methyl)phenyl-3,5-dinitro-N4,N4-di-n-propylsulfonilamide (42) was synthesized by the reaction of the sulfonyl chloride and 321 mg (3 mmol) of 4-methylaniline in 20 mL pyridine. The product was isolated by chromatography (hexane/EtOAc (6:1)) and crystallized using dichloromethane/hexane to obtain a yellow crystalline solid; yield 15.2%; mp.=103° C.; ¹H NMR (CDCl₃) δ 0.86 (m, 6H), 1.57 (m, 4H), 2.31 (s, 3H), 2.93 (t, 4H, J=7.44 Hz), 6.67 (bs, 1H), 6.90 (m, 2H, J=7.25 Hz), 7.03 (d, 1H, J=0.67 Hz), 7.19 (m, 1H), 8.11 (s, 2H); ¹³C NMR (CDCl₃) δ 11.03, 20.58, 21.28, 53.93, 119.08, 122.79, 127.25, 128.56, 129.16, 129.47, 135.04, 139.92, 141.57, 144.28. MS m/z 435.1 [M–H]⁻. Anal. ($C_{16}H_{24}N_4O_6S$) C, H, N.

Comparative Example K

N1-(3-Chloro)phenyl-3,5-dinitro-N4,N4-di-n-propylsulfonilamide (43) was synthesized by the reaction of the sulfonyl chloride and 351 mg (3 mmol) of 4-chloroaniline in 20 mL pyridine. The product was isolated by chromatography (hexane/EtOAc (6:1)) and crystallized by dichloromethane/hexane to obtain yellow crystals; yield 23.4%; mp.=108° C.; ¹H NMR (CDCl₃) δ 0.87 (t, 6H, J=7.25 Hz), 1.59 (m, 4H), 2.95 (t, 4H, J=7.43 Hz), 6.74 (s, 1H), 7.17 (m, 4H), 8.16 (s, 2H); ¹³C NMR (CDCl₃) δ 11.02, 20.57, 53.94, 119.46, 121.67, 126.37, 128.63, 130.73, 135.32, 136.44, 141.85, 144.26. MS m/z 455.1 [M–H]⁻. Anal. ($C_{18}H_{21}ClN_4O_6S$) C, H, N.

Comparative Example L

N1-(3,4-Dichloro)phenyl-3,5-dinitro-N4,N4-di-n-propylsulfonilamide (44) was synthesized by the reaction of the sulfonyl chloride and 486 mg (3 mmol) of 3,4-dichloro aniline in 20 mL pyridine. The product was isolated by chromatography (hexane/EtOAc (6:1)) and crystallized by dichloromethane/hexane to obtain a yellow crystalline solid; yield 264 mg, 54%; mp=111° C.; ¹H NMR (CDCl₃) δ 0.88 (m, 6H), 1.61 (m, 4H), 2.95 (m, 4H), 6.84 (bs, 1H), 7.01 (dd, 1H, J=2.50, 8.75 Hz)), 7.23 (d, 1H, J=2.50 Hz), 7.40 (d, 1H, J=8.75 Hz), 8.16 (s, 2H); ¹³C NMR (CDCl₃) δ 11.06, 20.63, 54.02, 120.64, 123.27, 128.27, 128.77, 130.16, 131.33, 133.61, 134.84, 142.04, 144.34. MS (FAB) m/z Calcd for $C_{18}H_{20}ClN_4O_6S$ (M+Na)⁺ 513.0378, Measured (M+Na)⁺ 513.0388. Anal. ($C_{18}H_{22}N_4O_6S$) C, H, N.

Comparative Example M

N1-(3,5-Dichloro)phenyl-3,5-dinitro-N4,N4-di-n-propylsulfonilamide (45) was synthesized by the reaction of the sulfonyl chloride and 486 mg (3 mmol) of 3,5dichloro aniline in 20 mL pyridine. The product was isolated by chromatography (hexane/EtOAc (6:1)) and crystallized by dichloromethane/hexane to obtain yellow crystals; yield 356 mg, 73%; mp=144° C.; ¹H NMR (CDCl₃) δ 0.87 (t, 6H, J=7.50 Hz), 1.63 (m, 4H), 2.95 (q, 4H, J=6.63 Hz), 6.69 (bs, 1H), 7.06 (d, 1H, J=0.17 Hz), 7.20 (d, 2H, J=0.17 Hz), 8.17 (d, 2H, J=0.25 Hz); $^{13}$C NMR (CDCl$_3$) δ 11.01, 20.58, 53.99, 119.28, 126.13, 128.14, 128.64, 136.02, 137.27, 142.02, 144.30. MS m/z 489.1 (M–H)$^-$. Anal. (C$_{18}$H$_{20}$ClN$_4$O$_6$S) C, H, N.

Comparative Example N

N1-(2-Pyridinyl)-3,5-dinitro-N4,N4-di-n-propylsulfonilamide (46) was synthesized by the reaction of the sulfonyl chloride and 564 mg (6 mmol) of 2-aminopyridine in 20 mL pyridine. The product was isolated by chromatography (hexane/EtOAc (1:1) and crystallized using dichloromethane/hexane to afford yellow crystals; yield 326 mg, 62%; mp=204° C.; $^1$H NMR (CDCl$_3$) δ 8 0.86 (t, 6H, J=7.50 Hz), 1.62 (m, 4H), 2.94 (m, 4H), 6.90 (m, 1H), 7.47 (d, 1H, J=8.00 Hz), 7.85 (m, 1H), 8.24 (m, 1H'), 8.31 (s, 2H), 8.65 (s, 1H); $^{13}$C NMR (CDCl$_3$) δ 11.17, 11.25, 20.65, 20.75, 53.67, 54.03, 114.02, 116.12, 127.94, 133.61, 138.62, 141.11, 144.12, 144.83, 155.69. MS m/z 424.0 (M+H)$^+$. Anal. (C$_{18}$H$_{22}$N$_4$O$_6$S) C, H, N.

The IC$_{50}$ values for the compounds of Examples 4–7 and Comparative Examples 8–21 against protozoan parasites and mammalian cells are summarized below:

| Compound | L. donovani axenic amastigotes[a,b] | T. b. brucei variant 221[b,c] | J774 macrophages[a,f] |
|---|---|---|---|
| 15 (10) | 20.1 ± 0.2 | 2.57 ± 0.70 | 8.43 ± 0.69 |
| 20 (11) | 5.03 ± 1.08 | 0.4 | 28.3 ± 3.8 |
| 30 (15) | 8.11 ± 3.33 | 0.5 | 25.3 ± 3.8 |
| 31 (20) | 10.6 ± 2.6 | 1.9 | 47.7 ± 1.6 |
| 32 (21) | 2.57 ± 0.25 | 0.1 | 11.9 ± 0.5 |
| 3 (Oryzalin) | 64.8 ± 3.6 | 11.4 ± 0.6 | 32.9 ± 1.6 |
| 33 (3) | >100 | 4.6 | Not tested |
| 34 (4) | >100 | 5.9 | Not tested |
| 35 (5) | >100 | 4.0 | Not tested |
| 36 (6) | 26.7 ± 0.4 | 10.2 | Not tested |
| 37 (7) | 54.3 ± 8.5 | 9.2 | Not tested |
| 38 (9) | 42.8 ± 2.3 | 2.5 | Not tested |
| 39 (12) | 31.9 ± 14.6 | 20.5 | 15.2 ± 6.7 |
| 40 (13) | 32.1 ± 12.7 | 10.5 | 10.5 ± 2.0 |
| 41 (14) | 13.3 ± 3.0 | 9.5 | 9.13 ± 3.81 |
| 42 (16) | 22.7 ± 0.8 | 0.92 | 15.8 ± 2.1 |
| 43 (17) | 5.47 ± 0.10 | 0.88 | 8.67 ± 0.17 |
| 44 (18) | 5.03 ± 0.80 | 6.7 | 7.19 ± 0.59 |
| 45 (19) | 3.71 ± 0.91 | 3.4 | 5.12 ± 0.35 |
| 46 (22) | 59.7 ± 6.2 | 10.9 | 44.9 ± 16.3 |
| Pentamidine | 2.00 ± 0.06 | 0.0194 ± 0.0069 | Not tested |
| Suramin | Not tested | 0.233 ± 0.050 | Not tested |

Example 8

IC$_{50}$ values for Compounds 3, 20, 37, 15, and 17 against several different protozoan parasites and mammalian cell lines were tested Chemicals and biochemicals. Where not otherwise indicated, commercial materials were obtained from Sigma. Dinitroaniline sulfonamides were synthesized as outlined above. Ansamitocin P3 was obtained from the drug inventory of the National Cancer Institute.

Determination of the drug susceptibility of parasites and mammalian cells. The susceptibility of Leishmania donovani amastigote-like parasites (WHO designation: MHOM/SD/62/1S-CL2$_D$) to growth inhibition by compounds of interest was measured in a three-day assay using the tetrazolium dye-based CellTiter reagent (Promega) (Werbovetz, K., Brendle, J., and Sackett, D. (1999) Mol. Biochem. Parasitol. 98, 53–65., and Havens, C., Bryant, N., Asher, L., Lamoreaux, L., Perfetto, S., Brendle, J., and Werbovetz, K. (2000) Mol. Biochem. Parasitol. 110, 223–236). The amastigote medium used in this assay is based on the medium mentioned by Joshi et al. (Joshi, M., Dwyer, D. M., and Nakhasi, H. L. (1993) Mol. Biochem. Parasitol. 58, 345–354). Prior to addition of fetal bovine serum to a final concentration of 20%, this amastigote medium contains 15 mM KCl, 115 mM KH$_2$PO$_4$, 10 mM K$_2$HPO$_4$, 0.5 mM MgSO$_4$, 24 mM NaHCO$_3$, a 1-concentration of RPMI-1640 vitamins and amino acids, 2.0 mM L-glutamine, 22 mM D-glucose, 100 units/mL penicillin, 100 ∝g/ml streptomycin, 0.1 mM adenosine, 1 ∝g/mL folate, and 25 mM MES (pH 5.5). Compounds were tested for their activity against bloodstream-form Trypanosoma brucei brucei (MITat 1.2, variant 221) axenically-cultured in HMI-9 medium , H., and Hirumi, K. (1989) J. Parasitol. 75, 985–989.) following the procedure of Ellis et al. (Ellis, J., Fish, W., Sileghem, M., and McOdimba, F. (1993) Vet. Parasitol. 50, 143–149.) with some modifications. Briefly, 100 µL of late log phase parasites were incubated in 96-well plates (Costar) at an initial concentration of 10$^5$ cells/ml with or without test compounds at 37° C. in a humidified 5% CO$_2$ atmosphere for 72 hours. Twenty-five µL of a 5 mg/mL solution of MTT (prepared in phosphate buffered saline and filter sterilized) was then added to each well and plates were re-incubated at 37° C. as before for 2 h. One hundred ∝L of 20% SDS lysis buffer (prepared in 50% aqueous DMF) was added to each well and plates were incubated as before for an additional 3–4 h. Optical densities were then measured at 570 nm using SpectraMax Plus microplate reader. IC$_{50}$ values, the concentration of the compound that inhibited cell growth by 50% compared to untreated control were determined with the aid of the software program SoftMax Pro (Molecular Devices). This program uses the dose-response equation y=((a–d)/(1+(x/c)$_b$))+d, where x=the drug concentration, y=absorbance at 490 nm, a=upper asymptote, b=slope, c=IC$_{50}$ and d=lower asymptote. Assessment of the in vitro sensitivity of T. b. brucei Lab 110 EATRO and P. falciparum strains to compounds was performed by methods described in Donkor et al. (Donkor, I., Assefa, H., Rattendi, D., Lane, S., Vargas, M., Goldberg, B., and Bacchi, C. (2001) Eur. J. Med. Chem. 36, 531–538.) and Guan et al. (Guan, J., Kyle, D., Gerena, L., Zhang, Q., Milhous, W., and Lin, A. (2002) J. Med. Chem. 45, 2741–2748).

The toxicity of compounds to J774 murine macrophages and PC3 colon carcinoma cells was measured in a three-day assay using the CellTiter reagent. J774 macrophages in DMEM medium supplemented with 10% heat inactivated fetal calf serum, 2.0 mM L-glutamine, 50 units/mL penicillin, and 50 µg/mL streptomycin were added to individual wells of a 96well plate at a concentration of 10$_4$ cells/L and a total volume of 100 µL. Macrophages were allowed to adhere for 24 hours, then the medium was removed and replaced with serial dilutions of the test compounds in the DMEM medium mentioned above without phenol red. After 72 hr incubation with the test compounds at 37° C. in a humidified 5% CO$_2$ incubator, cell viability was determined using the CellTiter reagent by adding 20 µL of assay solution to each well. After a 6–7 h incubation at 37° C. to allow for color development, the absorbance of each well at 490 nm was measured in a SpectraMax Pro microplate reader (Molecular Devices). The toxicity of compounds to PC3 cells was assessed in the same manner as for the macrophages, except that the medium used was RPMI 1640 supplemented with 10% heat inactivated fetal calf serum, 2.0 mM L-glutamine, 50 units/mL penicillin, and 50 ∝g/mL streptomycin. IC$_{50}$ values for the J774 and PC3 assays were determined with the software program SoftMax Pro as described earlier.

TABLE 4

IC$_{50}$ Values for various Compounds (μM) Against Protozoan Parasites and Mammalian Cell Lines

| Compound | L. donovani axenic amastigotes[a,b] | T. b. brucei variant 221[b,c] | T. b. brucei Lab 110 EATRO[d] | P. falciparum D6 strain[e] | P. falciparum W2 strain[e] | J774 macrophages[a] | PC3 prostate[a,f] |
|---|---|---|---|---|---|---|---|
| 3 | 72.5 ± 23.9 | 11.4 ± 0.6 | 5.0 | 4.0 | 3.6 | 32.9 ± 1.6 | 57.8 ± 10.4 |
| 20 | 5.41 ± 0.89 | 0.412 ± 0.044 | 0.58 | 11 | 13 | 30.8 ± 1.9 | 41.3 ± 8.5 |
| 37 | 56.9 ± 3.4 | 8.06 ± 0.64 | 3.0 | 13 | >25 | 21.8 ± 2.1 | 40.5 ± 8.6 |
| 15 | 20.1 ± 0.2 | 2.57 ± 0.70 | 1.8 | 5.1 | 4.3 | 8.43 ± 0.69 | 17.2 ± 2.8 |
| 17 | 11.7 ± 0.7 | 9.48 ± 1.73 | 5.6 | 10 | 12 | 1.91 ± 0.36 | 11.2 ± 1.3 |

[a]Values represent the mean ± SD of at least two independent experiments
[b]IC50 values determined by tetrazolium dye assay after three-day incubation with test compounds. The starting concentration of cells was 106 parasites/ml
[c]IC50 values determined by tetrazolium dye assay after three-day incubation with test compounds. The starting concentration of cells was 105 parasites/ml
[d]IC50 values determined by Coulter counter after two-day incubation with test compounds as described in Donkor et al. (21) The starting concentration of cells was 105 parasites/ml
[e]IC50 values determined by tritiated hypoxanthine uptake as described in Guan et al. (22). At the start of the experiment, erythrocytes were at 0.2% parasitemia and 1% hemotocrit.
[f]IC50 values determined by tetrazolium dye assay after three-day incubation with test compounds. The starting concentration of cells was 104 cells/ml As used herein, the term "treatment" includes partial or total inhibition or retardation of the undesirable proliferating parasites with minimal inhibition or retardation of normal cells in the vertebrate host. Without limiting the scope of the present invention, a desired mechanism of treatment is the selective binding of the compounds of the present invention with the tubulin of the protozoan with minimal or no binding to the tubulin of the subject being treated. Preferably, the compounds of the present invention will be bind parasitic tubulin versus mammalian tubulin more selectively than oryzalin. Preferably, the compounds of the present invention will also be less toxic to normal cells than oryzalin.

The terms "therapeutically effective" and "pharmacologically effective" are intended to qualify the amount of each agent which will achieve the goal of improvement in disease severity and the frequency of incidence, while avoiding adverse side effects typically associated with alternative therapies.

The dosage form and amount can be readily established by reference to known treatment regiments. The amount of therapeutically active compound that is administered and the dosage regimen for treating a disease condition caused by parasitic protozoa with the compounds and/or compositions of this invention depends on a variety of factors, including the age, weight, sex, and medical condition of the subject, the severity of the disease, the route and frequency of administration, and the particular compound employed, the particular protozoa causing the disease, as well as the pharmacokinetic properties of the individual treated, and thus may vary widely. Such treatments may be administered as often as necessary and for the period of time judged necessary by the treating physician. One of skill in the art will appreciate that the dosage regime or therapeutically effective amount of the inhibitor to be administrated may need to be optimized for each individual. The pharmaceutical compositions may contain active ingredient in the range of about 0.1 to 2000 mg, preferably in the range of about 0.5 to 500 mg and most preferably between about 1 and 200 mg. A daily dose of about 0.01 to 100 mg/kg body weight, preferably between about 0.1 and about 50 mg/kg body weight, may be appropriate. The daily dose can be administered in one to four doses per day.

The dinitroaniline sulfonamide compounds of the present invention may be administered by any suitable route known to those skilled in the art, preferably in the form of a pharmaceutical composition adapted to such a route, and in a dose effective for the treatment intended. The pharmaceutical composition comprises a therapeutically effective amount of a compound of Formula I or II, or a derivative or pharmaceutically acceptable salt or ester thereof in association with at least one pharmaceutically acceptable carrier, adjuvant, or diluent (collectively referred to herein as "carrier materials") and, if desired, other active ingredients. The active compounds of the present invention may be administered by any suitable route known to those skilled in the art, preferably in the form of a pharmaceutical composition adapted to such a route, and in a dose effective for the treatment intended( The active compounds and composition may, for example, be administered orally, intra-vascularly, intraperitoneally, intranasal, intrabronchial, subcutaneously, intramuscularly or topically (including aerosol).

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable carrier.

For intravenous, intramuscular, subcutaneous, or intraperitoneal administration, the compound may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

Formulations suitable for parenteral administration conveniently comprise a sterile aqueous preparation of the active compound which is preferably made isotonic. Preparations for injections may also be formulated by suspending or emulsifying the compounds in non-aqueous solvent, such as vegetable oil, synthetic aliphatic acid glycerides, esters of higher aliphatic acids or propylene glycol.

Formulations for topical use include known gels, creams, oils, and the like. For aerosol delivery, the compounds may be formulated with known aerosol excipients, such as saline, and administered using commercially available nebulizers. Formulation in a fatty acid source may be used to enhance biocompatibility.

The term "subject" for purposes of treatment includes any human or animal subject who is affected with a disease caused by parasitic protozoa, specifically *Leishmania donovani*, and also including *Trypanosoma cruzi, Trypanosoma brucie gambiense, Trypanosoma brucie rhodesiense, Plasmodium falciparum, Plasmodium vivax, Plasmodium ovali*, and *Plasmodium malariae*. Such diseases include leishmaniasis, including visceral leishmaniasis, mucocutaneous leishmaniasis, and cutaneous leishmaniasis; Chagas disease; human African trypanosomiasis, also known as African sleeping sickness; animal trypanosomiasis; and malaria. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

Derivatives are intended to encompass any compounds which are structurally related to the dinitroaniline compounds of formulae I and II and have the ability to bind to parasite tubulin at least as well as oryzalin. In accordance with the present invention, the derivatives should also bind to the parasitic tubulin with more affinity than to vertebrate tubulin. The derivatives should bind to the tubulin of one or more of the parasites selected from *Leishmania donovani, Trypanosoma cruzi, Trypanosoma brucie gambiense, Trypanosoma brucie rhodesiense, Plasmodium falciparum, Plasmodium vivax, Plasmodium ovali*, and *Plasmodium malariae*. By way of example, such compounds may include, but are not limited to, prodrugs thereof. Such compounds can be formed in vivo, such as by metabolic mechanisms.

The present invention also relates to therapeutic methods of treating patients who have diseases caused by the above protozoa, which include leishmaniasis, including visceral leishmaniasis, mucocutaneous leishmaniasis, and cutaneous leishmaniasis; Chagas disease; human African trypanosomiasis, also known as African sleeping sickness; animal trypanosomiasis; and malaria The methods comprise administering a therapeutically effective amount of a compound of formula I, II or III to a subject having one of these disorders.

Also included in the family of compounds of formulae I, II and III are the pharmaceutically acceptable salts thereof. The phrase "pharmaceutically acceptable salts" connotes salts commonly used to form alkali metal salts and to form addition salts of free acids or free bases. The nature of the salt is not critical, provided that it is pharmaceutically acceptable. Suitable pharmaceutically acceptable acid addition salts of compounds of formulae I and II may be prepared from an inorganic acid or from an organic acid Examples of such inorganic acids are hydrochloric, hydrobromic, hydroiodic, nitric, carbonic, sulfuric, and phosphoric acid. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucoronic, maleic, fumaric, pyruvic, aspartic, glutamic, benzoic, anthranilic, mesylic, salicylic, p-hydroxybenzoic, phenylacetic, mandelic, ambonic, pamoic, methanesulfonic, ethanesulfonic, benzenesulfonic, pantothenic, 2-hydroxyethanesulfonic, toluenesulfonic, sulfanilic, cyclohexylaminosulfonic, stearic, algenic, β-hydroxybutyric, galactaric, and galacturonic acids. Suitable pharmaceutically acceptable base addition salts of compounds of formulae I, II, and III include metallic salts made from aluminum, calcium, lithium, magnesium, potassium, sodium, and zinc. Alternatively, organic salts made from N,N'-dibenzylethylenediamine, chloroprocaine, choline, diethanolamine, ethylenediamine, meglumine (N-methylglucamine) and procaine may be used form base addition salts of the compounds of formulae I and II. All of these salts may be prepared by conventional means from the corresponding compounds of formulae I, II, and III by reacting, for example, the appropriate acid or base with the compound of formula I, II, or III.

Where the term "alkyl" is used, it includes $C_1$ to $C_{10}$ linear or branched alkyl radicals, examples include methyl, ethyl, propyl, isopropyl, butyl, tert-butyl, and so forth. The term "aryl" includes such aromatic radicals as phenyl, biphenyl, and benzyl, as well as fused aryl radicals such as naphthyl, anthryl, phenanthrenyl, fluorenyl, and indenyl and so forth. The term "aryl" also encompasses "heteroaryls," which are aryls that have carbon and one or more heteroatoms, such as O, N, or S in the aromatic ring. Examples of heteroaryls include indolyl, pyrrolyl, and so on. The term "alkylaryl" encompasses aryl radicals that have an alkyl substituent at any substitutable position. The terms "haloaryl" and "haloalkyl" encompass aryls and alkyls, respectively, having one or more halogen (F, Cl, Br, or I) atoms substituted to the aryl or allyl at any substitutable position.

All documents referenced herein are incorporated by reference.

Although this invention has been described with respect to specific embodiments, the details of these embodiments are not to be construed as limitations.

REFERENCES

1. World Health Organization. 2000, www.who.int/inf-fs/en/fact116.html.
2. Berman, J. D. Clin. Infect. Dis. 1997, 24, 684–703.
3. Lira, R; Sundar, S.; Makharia, A.; Kenney, R; Gam, A.; Saraiva, E.; Sacks, D. *J. Infect. Dis.* 1999, 180, 564–567.
4. Morejohn, L.; Fosket, D. *Pharmac. Ther.* 1991, 51, 217–230.
5. Chan, M. M.-Y.; Fong, D. *Science* 1990, 249, 924–926.
6. Chan, M. M.-Y.; Grogl., M.; Chen, C.-C.; Bienen, E. J.; Fong, D. *Proc. Natl. Acad. Sci. USA* 1993, 90, 5657–5661.
7. Callahan, H. L.; Kelley, C.; Pereira, T.; Grogl, M. *Antimicrob. Agents Chemother.* 1996, 40, 947–952.
8. Werbovetz, K.; Brendle, J.; Sackett, D. *Mol. Biochem. Parasitol.* 1999, 98, 53–65.
9. Benbow, J.; Bernberg, E.; Korda, A.; Mead, J. *Antimicrob. Agents Chemother.* 1998, 42,339–343.
10. Armson, A.; Kamau, S.; Grimm, F.; Reynoldson, J.; Best, W.; MacDonald, L.; Thompson, R. *Acta Tropica* 1999, 73, 303–311.
11. Chan, M. M.-Y.; Triemer, R. E.; Fong, D. *Differentiation* 1991, 46, 15–21.
12. Schultz, H. In *Organic Syntheses*; Rabjohn, N., Ed.; John Wiley & Sons, Inc.: New York, 1963; Collective Vol. IV, pp 364–366.
13. Judkins, B.; Allen, D.; Cook, T.; Evans, B.; Sardharwala, T. *Synth. Comm.* 1996, 26, 4351–4367.
14. Havens, C.; Bryant, N.; Asher, L.; Lamoreaux, L.; Perfetto, S.; Brendle, J.; Werbovetz, K. *Mol. Biochem. Parasitol.* 2000, 110, 223–236.

15. Chan, M. M.-Y.; Tzeng, Y.; Emge, T. J.; Ho, C.-T.; Fong, D. *Antimicrob. Agents Chemother.* 1993, 37, 1909–1913.
16. Bai, R.; Lin, C.; Nguyen, N.; Liu, T.; Hamel, E. *Biochemistry* 1989, 28, 5606–5612.
17. Shan, B.; Medina, J.; Santha, E.; Frankmoelle, W.; Chou, T.; Learned, R; Narbut, M.; Stott, D.; Wu, P.; Jaen, J.; Rosen, T.; Timmermans, P.; Beckmann, H. *Proc. Natl. Acad. Sci. USA* 1999, 96, 5686–5691.
18. Morejohn, L.; Bureau, T.; Mole-Bajer, J.; Bajer, A.; Fosket, D. *planta* 1987, 172, 252–264.

The invention claimed is:

1. A compound of Formula I useful for the treatment of diseases caused by parasitic protozoa comprising:

I wherein $R^1$ and $R^2$ can be the same or different and are selected from the group consisting of H and $C_1$–$C_{10}$ alkyl, provided that $R_1$ and $R_2$ are not both n-propyl, not H and n-propyl, and not H and 3-pentyl, or $R_1$ and $R_2$ can form a 5 or 6 membered ring containing C, N, and O, provided that the ring is not morpholino or piperydinyl; and $R^3$ is a sulfonamide;

wherein the nitrogen atom of $R^3$ can substituted with $C_1$–$C_{10}$ alkyl, aryl, alkylaryl, alkoxyaryl, or haloaryl.

2. The compound of claim 1 wherein $R^1$ and $R^2$ are selected the group consisting of methyl, ethyl, and butyl and combinations thereof.

3. The compound of claim 1 wherein $R^1$ and $R^2$ together form pyrrolidino.

4. The compound of claim 1 wherein the compound is useful for the treatment of diseases caused by parasitic protozoa, wherein the disease is visceral leishmaniasis, mucocutaneous leishmaniasis, cutaneous leishmaniasis, Chagas disease; human African trypanosomiasis, animal trypanosomiasis; or malaria.

5. The compound of claim 1 wherein the compound is less cytotoxic to normal cells than oryzalin.

6. A compound of Formula II useful for the treatment of diseases caused by parasitic protozoa comprising:

II wherein $R_4$ and $R_5$ are the same and selected from the group consisting of $C_1$–$C_{10}$ alkyl, or $R_4$ and $R_5$ form a pyrrolidine ring;

and $R_6$ is selected from the group consisting of $C_1$–$C_{10}$ alkyl, aryl, alkylaryl, alkoxyaryl, and haloaryl wherein the compound is less cytotoxic to normal cells than oryzalin.

7. The compound of claim 6 wherein $R^6$ is selected from the group consisting of methyl, ethyl, propyl, butyl, isopropyl, phenyl, methoxyphenyl, ethoxyphenyl, propoxyphenyl, methylphenyl, ethylphenyl, propylphenyl, butylphenyl, chloropheneyl, dichlorophenyl, fluorophneyl, difluorophenyl, and pyridnyl.

8. The compound of claim 6 wherein $R^4$ and $R^5$ are selected from the group consisting of methyl, ethyl, propyl, butyl, pentyl, and hexyl.

9. The compound of claim 6 wherein the compound is useful for the treatment of diseases caused by parasitic protozoa, wherein the disease is leishmaniasis, Chagas disease; human African trypanosomiasis, animal trypanosomiasis; or malaria.

10. A compound of Formula III useful for the treatment of diseases caused by parasitic protozoa comprising:

III wherein n is 1, 2, 3, or 4; and

Y is selected from the group consisting of $NH_2$, $C_6H_5NH$, $C_6H_4(OCH_3)NH$, $C_6H_4(CH_3)NH$, $C_6H_4ClNH$, provided that when n=2 Y is not $NH_2$.

11. The compound of claim 10 wherein the compound is selected from the group consisting of N1-Phenyl-3,5-dinitro-N4,N4-di-n-propylsulfonilamide; N1-(3-Methoxy)phenyl-3,5-dinitro-N4,N4-di-n-propylsulfonilamide; N1-(3-Methyl)phenyl-3,5-dinitro-N4,N4-di-n-propylsulfonilamide; N1-Phenyl-3,5-dinitro-N4,N4-di-n-ethylsulfonilamide; and N1-Phenyl-3,5-dinitro-N4,N4-di-n-butylsulfonilamide.

12. The compound of claim 10 wherein the compound is used to treat diseases caused by *L. donovani*.

13. The compound of claim 12 wherein the compound is selected from the group consisting of N1-Phenyl-3,5-dinitro-N4,N4-di-n-propylsulfonilamide; N1-(3-Methoxy)phenyl-3,5-dinitro-N4,N4-di-n-propylsulfonilamide; and N1-Phenyl-3,5-dinitro-N4,N4-di-n-butylsulfonilamide.

14. The compound of claim 10 wherein the compound is used to treat diseased caused by *T.b. brucei*.

15. The compound of claim 14 wherein the compound is selected from the group consisting of N1-Phenyl-3,5-dinitro-N4,N4di-n-propylsulfonilamide; N1-(3-Methoxy)phenyl-3,5-dinitro-N4,N4-di-n-propylsulfonilamide; N1-(3-Methyl)phenyl-3,5-dinitro-N4,N4-di-n-propylsulfonilamide; N1-Phenyl-3,5-dinitro-N4,N4-di-n-ethylsulfonilamide; and N1-Phenyl-3,5-dinitro-N4,N4-di-n-butylsulfonilamide.

16. The compound of claim 10 wherein the compound is less cytotoxic to normal cells than oryzalin.

17. A method of treating subjects having diseases caused by parasitic protozoa, the method comprising administering a therapeutically effective amount of a compound of claim 1, 6, or 10 to a subject in need of such treatment.

18. The method of claim 17 wherein the disease caused by parasitic protozoa is selected from visceral leishmaniasis, mucocutaneous leishmaniasis, and cutaneous leishmaniasis, Chagas disease; human African trypanosomiasis, animal trypanosomiasis; and malaria.

19. The method of claim 18 wherein the disease caused by parasitic protozoa is selected from visceral leishmaniasis, mucocutaneous leishmaniasis, and cutaneous leishmaniasis.

20. The method of claim 17 wherein the subject is a person.

* * * * *